United States Patent [19]

Franklin

[11] Patent Number: 4,613,709

[45] Date of Patent: Sep. 23, 1986

[54] PROCESS FOR THE PYROLYTIC DEHYDROCHLORINATION OF HALOALKANES IN THE PRESENCE OF AN INITIATOR BASED ON CHLORINATED PRODUCT AND THE INITIATOR EMPLOYED IN SUCH A PROCESS

[75] Inventor: James Franklin, Brussels, Belgium

[73] Assignee: Solvay & Cie., Brussels, Belgium

[21] Appl. No.: 765,966

[22] Filed: Aug. 15, 1985

[30] Foreign Application Priority Data

Aug. 20, 1984 [FR] France ................................ 8413050

[51] Int. Cl.4 ............................................ C07C 17/34
[52] U.S. Cl. ................................... 570/227; 570/228; 570/156
[58] Field of Search ........................ 570/227, 156, 228

[56] References Cited

FOREIGN PATENT DOCUMENTS 1210800 2/1966 Fed. Rep. of Germany ...... 570/227
947324 1/1949 France ............................... 570/227

Primary Examiner—Natalie Trousof
Assistant Examiner—Joseph A. Boska
Attorney, Agent, or Firm—Spencer & Frank

[57] ABSTRACT

The pyrolytic dehydrochlorination of haloalkanes is carried out with an initiator comprising chiefly decachlorobutane and octachloro-1-butene.

The process can be applied particularly to the production of chloroethylenes from the corresponding polychloroethanes.

9 Claims, No Drawings

PROCESS FOR THE PYROLYTIC DEHYDROCHLORINATION OF HALOALKANES IN THE PRESENCE OF AN INITIATOR BASED ON CHLORINATED PRODUCT AND THE INITIATOR EMPLOYED IN SUCH A PROCESS

The present invention relates to a process for the pyrolytic dehydrochlorination of haloalkanes in the presence of an initiator based on chlorinated product and to an initiator for the pyrolytic dehydrochlorination of haloalkanes, employed in such a process.

It is known from French Pat. No. 947,324 that the pyrolytic dehydrochlorination of haloalkanes, particularly of dichloroethane, tetrachloroethane, 1,1,2-trichloroethane and dichloropropane, may be catalysed or initiated by the addition of small quantities of chlorine or of a substance supplying chlorine at a high temperature, for example hexachloroethane.

It is also known from the document DE-B-1,210,800 to manufacture vinyl chloride by the pyrolytic dehydrochlorination of dichloroethane at 500°-620° C. at an absolute pressure of 3-20 atmospheres (3.06-20.4 bars) in the presence of 0.5-2% by weight of an initiator consisting of a chlorinated hydrocarbon such as hexachloroethane, carbon tetrachloride or perchloroethylene, excluding chlorinated hydrocarbons containing more than two carbon atoms per molecule, in order to avoid the formation of by-products.

These known processes have certain disadvantages. Chlorine reacts virtually completely with the compound which is to be dehydrochlorinated, which leads to the formation of undesired by-products and reduces the selectivity. Thus, in the case of the pyrolytic dehydrochlorination of 1,2-dichloroethane, the chlorine introduced as an initiator converts the dichloroethane principally to 1,1,2-trichloroethane and to 1,1- and 1,2-dichloroethylenes. Furthermore, below 350° C. the chlorinated hydrocarbons which are known as initiators give only low degrees of pyrolysis (=degrees of conversion of the haloalkane to the corresponding unsaturated compound). To increase these degrees of pyrolysis it becomes necessary to operate at high temperature, which consequently increases the energy costs and gives rise to the formation of by-products and of carbon. The latter is deposited on the walls of the pyrolysis reactor, requiring, as a result, stoppages at regular intervals for its cleaning.

The aim of the present invention is to overcome these disadvantages by providing a new process for the pyrolytic dehydrochlorination of haloalkanes in the presence of a new initiator capable of operating at more moderate temperatures. In addition, the present invention makes it possible to exploit hexachloro-1,3-butadiene which is a toxic by-product, practically devoid of outlets, which up till now had to be destroyed by burning.

For this purpose the invention relates to a process for the pyrolytic dehydrochlorination of haloalkanes in the presence of an initiator based on chlorinated product, which comprises chiefly decachlorobutane or an octachlorobutene such as octachloro-1-butene and/or a mixture of these products. Preferably, the initiator based on chlorinated product results from the additive chlorination of hexachloro-1,3-butadiene.

The invention also relates to an initiator based on chlorinated product for the pyrolytic dehydrochlorination of haloalkanes which results from the additive chlorination of hexachloro-1,3-butadiene and which comprises chiefly decachlorobutane and/or an octachlorobutene such as octachloro-1-butene, according to the degree to which the additive chlorination has advanced.

A chlorinated product is understood to be the product(s) resulting from the additive chlorination of hexachloro-1,3-butadiene which can be obtained in a manner known per se, for example by photochlorination or by iron-catalysed liquid-phase chlorination. When the additive chlorination of hexachlorobutadiene leads to the formation of product mixtures, these mixtures contain, in addition to the main products referred to above, a little hexachloroethane and possibly unconverted hexachloro-1,3-butadiene as well as a small proportion of various other products. When the additive chlorination of hexachlorobutadiene leads to the formation of a single chlorinated product, this is usually an octachlorobutene such as octachloro-1-butene or decachlorobutane.

The formation of a mixture of products or of a single chlorinated product depends particularly on the degree of chlorination of hexachlorobutadiene, on the temperature and the nature of the catalyst.

It is obvious, however, that a mixture of chlorinated products resulting from the additive chlorination of hexachloro-1,3-butadiene means not only the mixtures originating directly from the chlorination but also the mixtures which have undergone some modifications after the chlorination, such as those resulting from distillation or rectification operations and crystallisation operations, which make it possible to obtain an enrichment in one or other of the components of the mixture.

Lastly, insofar as the single chlorinated product is concerned, usually originating from the additive chlorination of hexachloro-1,3-butadiene, which may be employed in the process of the invention, it is also obvious that its origin is not critical per se for the pyrolytic dehydrohalogenation process of the invention and that this single product may originate from any starting material other than hexachloro-1,3-butadiene.

By way of example, the composition, in g/kg, of two crude mixtures resulting from the photochlorination of hexachloro-1,3-butadiene, as described in Example 2 below, is given below:

|  | Mixture A | Mixture B |
| --- | --- | --- |
| Octachloro-1-butene | 415 | — |
| Decachlorobutane | 303 | 812 |
| Hexachloroethane | 183 | 147 |
| Hexachloro-1,3-butadiene | 77 | <0.5 |
| Other, unidentified products | 22 | 41 |

These crude product mixtures and, similarly, some constituents of these mixtures, may be employed in the process according to the invention in a weight quantity which is usually between 0.01 and 10% and preferably between 0.1 and 5% relative to the haloalkane subjected to the pyrolytic dehydrochlorination. Satisfactory results have been obtained with weight quantities of mixture A and mixture B in the region of 1% relative to the haloalkane subjected to the pyrolytic dehydrochlorination. Satisfactory results have also been obtained by using, respectively, 1% by weight of octachloro-1-butene and 1% by weight of decachlorobutane relative to the weight of the haloalkane.

The initiators based on chlorinated product according to the invention have a very powerful accelerating effect in the temperature regions well below those which are required when known initiators are employed. Thus, in the case of the pyrolysis of gaseous 1,2-dichloroethane at atmospheric pressure, useful degrees of pyrolysis are obtained already at temperatures of 300° to 425° C. with the crude mixtures from the additive chlorination of hexachloro-1,3-butadiene employed in a proportion of 1% by weight relative to 1,2-dichloroethane. These degrees of pyrolysis naturally increase with the rise in temperature but at the cost of the appearance of secondary reactions, which give rise to the formation of undesirable by-products. The process according to the invention consequently makes it possible to choose a compromise solution via the temperature level of the pyrolysis.

From the work published by P. J. Thomas in Current Topics in Mass Spectrometry, Chem. Kinet. Proc. Symp. 1981, pages 115 to 140 (Chemical Abstracts 97, 197708u) it follows that, in the case of the pyrolysis of 1,2-dichloroethane, the degrees of formation of the main by-products such as acetylene, 1-chloro-1,3-butadiene and 2-chloro-1,3-butadiene, relative to the vinyl chloride produced, increase with the degree of pyrolysis, on the one hand, and with the temperature, on the other hand. As a result, the chief advantages contributed by the process according to the invention, relative to the unitiated process, can be summarised as follows:

(1) At a given degree of pyrolysis and output, the temperature of the pyrolytic dehydrochlorination can be lowered (resulting in an energy saving) and the selectivity, and consequently the yield, can be improved.

(2) At a given temperature and output it is possible to operate at a higher degree of pyrolysis, which reduces the proportion of haloalkanes to be recycled and thereby contributes an energy saving.

(3) At a given temperature and degree of pyrolysis, the output and the productiveness can be increased.

(4) The abovementioned advantages may be combined; for example, at a given output, but at a reduced temperature and an increased degree of pyrolysis, it is possible to obtain an energy saving without loss of selectivity.

An important advantage of the process according to the invention lies, consequently, in the fact that it can be applied at temperatures which are lower than those which can be used in the processes of the prior art. Temperatures between 200° and 450° C. have given satisfactory results for the various haloalkanes examined.

Another advantage of the process according to the invention lies in the fact that it may be employed either at atmospheric pressure or at a higher pressure. Preferably, the process is operated at atmospheric pressure or at a moderate pressure.

A moderate pressure is understood to mean pressures below 20 atmospheres (20.4 bars). Satisfactory results have been obtained at pressures between 1 and 15 bars.

The process for the pyrolytic dehydrochlorination of haloalkanes according to the invention may be applied to a large number of reactions. In particular, the following applications can be mentioned, without any restriction being intended:

manufacture of vinyl chloride from 1,2-dichloroethane manufacture of vinylidene chloride and of cis and trans 1,2-dichloroethylene from 1,1,2-trichloroethane manufacture of trichloroethylene from 1,1,2,2-tetrachloroethane manufacture of vinylidene fluoride from 1-chloro-1,1-difluoroethane.

The process according to the invention may also be applied when the pyrolytic dehydrochlorination of the haloalkane is combined with a substitutive chlorination of the product originating from the pyrolysis, that is to say in the case of a chlorination pyrolysis. Thus, the process according to the invention finds an application particularly for the manufacture of trichloroethylene and of perchloroethylene by chlorination pyrolysis of 1,2-dichloroethane alone or mixed with other chlorinated hydrocarbons.

It has also been found that, in order to reduce the overheating of the reaction mixture to a minimum, it may be desirable in some cases to carry out the pyrolytic dehydrochlorination reaction in the presence of additives which act as diluents but which are inert towards the reactants and the initiators involved in the reaction. As additives, use is preferably made of aliphatic chlorinated derivatives such as carbon tetrachloride or inorganic products such as hydrogen chloride or nitrogen. Preferably, the operation is carried out with carbon tetrachloride.

In general, the halogenated organic additives are added to the reaction mixture in a proportion of 1 to 25 moles per mole of haloalkane employed.

The process according to the invention may be carried out in any apparatus or any reactor which enables the operating conditions described above to be obtained simultaneously.

The following examples are given by way of explanation of the process according to the invention.

EXAMPLE 1

A series of tests was carried out to illustrate the effectiveness of the products of the additive chlorination of hexachloro-1,3-butadiene, namely, respectively, the crude mixtures A and B referred to above, octachloro-1-butene and decachlorobutane, as initiators for the pyrolytic dehydrochlorination of 1,2-dichloroethane. These tests were carried out at atmospheric pressure in a tubular reactor made of quartz containing carbon, 260 mm in length and with an inner diameter of 12.2 mm, preceded by a coaxial preheater, also made of quartz containing carbon, 170 mm in length and with an inner diameter of 8.1 mm, the whole system containing throughout its length an axial thermocouple sheath with an outer diameter of 6 mm (reactor volume=23 cm$^3$; preheater volume=2.0 cm$^3$). Electrical resistors wound onto the reactor permit a uniform temperature profile to be maintained throughout its length. The reactor is supplied with liquid 1,2-dichloroethane (purity>99.98%) at a constant and known rate, by means of a metering pump. Before entering the reactor, the dichloroethane is vaporised in the preheater, which has a temperature gradient between ambient temperature and the reaction temperature. In the case of the tests carried out in the presence of a pyrolysis initiator, the latter is dissolved beforehand in the 1,2-dichloroethane. The gaseous mixture leaving the reactor is diluted with a stream of nitrogen to prevent the condensation of some constituents, freed from the HCl which it contains by bubbling through water and subjected to an analysis by gas phase chromatography in order to determine the degree of pyrolysis. Measurements were made of the degree of pyrolysis attained at various temperatures with the initiators based on chlorinated product according to the invention and, for comparison, with the initiators of the prior art and in the absence of initiators, the residence time (volume of the oven divided by the gas feed rate, at the test temperature) being kept approximately constant. The results of these tests are collated in Table 1 below, in which the tests have been grouped by the pyrolytic dehydrochlorination temperature regions. They clearly show the very powerful accelerating effect of the initiators based on chlorinated product according to the invention, to an extent which makes them particularly attractive when they are employed at a low temperature, for example between 200° and 450° C., and in the case where the pyrolytic dehydrochlorination of 1,2-dichloroethane is carried out in gaseous phase, when they are employed between 300° and 425° C.

As initiators of the prior art, use has been made of carbon tetrachloride, perchloroethylene, hexachloroethane, and as another reference test, use has been made of a synthetic mixture representing the impurities (products other than octachloro-1-butene and decachlorobutane) present in mixture A. The numbers of the comparative tests in Table 1 are followed by the letter R.

It can be seen that carbon tetrachloride, perchloroethylene and hexachloroethane, employed separately at the temperatures at which the initiators based on chlorinated product according to the invention are already highly efficient (300° C.), produce no tangible result. Starting at 350° C. hexachloroethane gains some effectiveness, which remains inferior, however, to that of mixtures A or B and, in addition, it presents the disadvantage of leading to the formation of by-products containing three carbon atoms. As for the synthetic mixture representing the impurities present in the mixture A, this also remains low in efficiency, even at 425° C.

TABLE 1

| Test No. | Temperature °C. | Residence time, s | Initiator | Degree of pyrolysis, % | Observations |
|---|---|---|---|---|---|
| 1 | 302 | 10.0 | 1% by weight of mixture A | 43.2 | |
| 2 | 304 | 9.9 | 1% by weight of mixture B | 45.4 | |
| 3 | 304 | 10.3 | 1% by weight of octachloro-1-butene* | 32.4 | |
| 4 | 300 | 10.0 | 1% by weight of decachlorobutane* | 39.8 | — |
| 5R | 303 | 9.9 | 1% by weight of $C_2Cl_6$ | 0.7 | |
| 6R | 300 | 10.1 | 1% by weight of $CCl_4$ | 0.1 | |
| 7R | 349 | 10.5 | — | 1.8 | |
| 8 | 351 | 9.9 | 1% by weight of mixture A | 68.4 | |
| 9 | 350 | 10.6 | 1% by weight of mixture B | 60.5 | |
| 10 | 355 | 10.5 | 1% by weight of octachloro-1-butene | 72.1 | |
| 11 | 355 | 9.6 | 1% by weight of decachlorobutane | 59.3 | |
| 12R | 354 | 10.6 | 1% by weight of $C_2Cl_6$ | 32.2 | |
| 13R | 350 | 10.9 | 1% by weight of $CCl_4$ | 1.9 | |
| 14R | 350 | 10.1 | 0.18% by weight of $C_2Cl_6$ 0.08% by weight of $C_4Cl_6$ | 3.3 | This is a synthetic mixture representing 1% of mixture A minus its content of $C_4Cl_{10}$ and $C_4Cl_8$ (mixture A impurities). |
| 15R | 423 | 8.4 | — | 14.1 | Poorly reproducible results, probably due to wall effects. |
| 16R | 425 | 10.0 | — | 6.2 | |
| 17 | 427 | 9.6 | 1% by weight of mixture A | 82.5 | |
| 18 | 422 | 10.0 | 1% by weight of mixture B | 74.5 | |
| 19 | 426 | 10.1 | 1% by weight of octachloro-1-butene | 85.4 | |
| 20 | 433 | 10.2 | 1% by weight of decachlorobutane | 76.3 | |
| 21R | 426 | 10.2 | 1% by weight of $C_2Cl_6$ | 65.4 | |
| 22R | 427 | 10.8 | 0.18% by weight of $C_2Cl_6$ 0.08% by weight of $C_4Cl_6$ | 19.2 | Synthetic mixture as in test No. 14R (mixture A impurities) |
| 23R | 431 | 10.1 | 1% by weight of $C_2Cl_4$ | 15.8 | |
| 24R | 529 | 8.1 | — | 64.3 | |
| 25 | 529 | 8.1 | 1% by weight of mixture A | 98.5 | |

*Purities of octachloro-1-butene and of decachlorobutane > 99%.

EXAMPLE 2

In this example a description is given of the process employed for the photochlorination of hexachloro-1,3-butadiene with a view to obtaining the crude mixtures which can be employed as initiators of the pyrolytic dehydrochlorination reactions of haloalkanes.

The photochlorination reactor, made of pyrex glass, consists of three concentric vertical tubes. The actinic Lamp (Philips TL05, 120 W fluorescent tube) is placed axially inside the narrowest tube. The annular space, closed at the ends, between the latter and the second tube, forms the reaction zone. In the annular space between the second and the third tube, also closed at the ends, circulation of coolant enables the temperature in the reaction zone to be maintained at 3° C. (a stream of nitrogen sweeps the space between the lamp and the reactor to prevent the condensation of atmospheric moisture). The inner and outer diameters and the height of the reaction zone are, respectively, 55, 78 mm and 210 mm, which correspond to a volume of 505 cm$^3$. At the bottom of the reactor, a perforated ring-shaped injector enables gaseous chlorine to be introduced. The reactor is also fitted with a stopcock for draining and a tubing connecting the head of the reactor, via a reflux condenser, to a bubbler containing caustic soda.

600 g (3.90 mol) of carbon tetrachloride and 200 g (0.77 mol) of hexachloro-1,3-butadiene are introduced into the reactor. Gaseous chlorine is introduced at a rate of approximately 2.5 normal liters per hour.

After 26 h, the product is drained and washed with 2 N caustic soda (2×400 cm$^3$), and then with water (5×400 cm$^3$). After removal of CCl$_4$ in a rotary evaporator at 80° C. and at reduced pressure (5 torr), 230 g of mixture A are obtained.

When the photochlorination time is extended up to 56 h, 200 g of mixture B are obtained after washing the product and removing the CCl$_4$.

EXAMPLE 3

The procedure is as in Example 1 but with the use of 1,1,2,2-tetrachloroethane with a view to manufacturing trichloroethylene. The results obtained are summarised in Table 2 below.

TABLE 2

| Temperature °C. | Residence time s | Initiator | Degree of pyrolysis, %* |
|---|---|---|---|
| 351 | 10.5 | — | 4.3 |
| 353 | 10.1 | 1% by weight of mixture A | 75.8 |
| 304 | 12.3 | 1% by weight of mixture A | 61.6 |

*Calculated from the flow rates of 1,1,2,2-tetrachloroethane supplied and of hydrogen chloride formed.

EXAMPLE 4

The procedure is as in Example 1, but with the use of 1,1,2-trichloroethane with a view to manufacturing dichloroethylenes. The results obtained are summarised in Table 3 below.

TABLE 3

| Temperature °C. | Residence time s | Initiator | Degree of pyrolysis, %** |
|---|---|---|---|
| 424 | 11.6 | — | 2.7 |
| 424 | 10.3 | 1% by weight of mixture A | 36.7 |

**Calculated from the flow rates of 1,1,2-trichloroethane supplied and of hydrogen chloride formed.

EXAMPLE 5

In this example a description is given of the process employed for the iron-catalysed liquid-phase chlorination of hexachloro-1,3-butadiene with a view to producing the crude mixtures which can be employed as initiators of the pyrolytic dehydrochlorination reactions of haloalkanes.

Into a stainless steel stirred autoclave, 1.5 dm$^3$ in volume, equipped with heating by oil circulation through a double jacket, are introduced:

1190 g (4.60 mol) of hexachloro-1,3-butadiene of purity greater than 98% by weight, 1.34 g of anhydrous FeCl$_3$.

After the contents of the reactor have been heated to 125° C., liquid chlorine is added gradually from a measuring container maintained under nitrogen pressure. The rate of addition of chlorine is adjusted so as to maintain an absolute pressure of 9 bars in the reactor. The reaction is stopped after 10 h, when 652 g (9.20 mol) of chlorine have been added.

The reaction medium is stripped with nitrogen to remove the residual chlorine and then washed with 6 N HCl until the FeCl$_3$ has been removed. The product obtained has the following composition in g/kg:

| Mixture C | |
|---|---|
| Octachloro-1-butene | 200 |
| Decachlorobutane | 615 |
| Hexachloroethane | 128 |
| Hexachloro-1,3-butadiene | 25 |
| Other unidentified products | 32 |

EXAMPLE 6

In this example a description is given of a process for the pyrolytic dehydrochlorination of 1,2-dichloroethane and of its substitutive chlorination products. This process is also called chlorination pyrolysis of 1,2-dichloroethane. The initiator employed in this example is the mixture C described in Example 5 above.

The chlorination pyrolysis of 1,2-dichloroethane in gaseous phase has been carried out at atmospheric pressure in a spherical continuous mixer reactor of approximately 1 dm$^3$, made of pyrex, self-stirred by gas jets (cf. Chem. Eng. Sci., 1973, 28, p. 129–137), the reactants being added in gaseous form by means of an injector with four tuyeres placed in the middle of the sphere. The reactor is placed in an enclosure inside which air is heated electrically and stirred by means of a turbine, in order to maintain the required reaction temperature. 1,2-Dichloroethane and the diluent (CCl$_4$) intended to moderate the heat effect of the reaction are supplied through a vertical tube evaporator which is heated by electricity and connected to the reactor injector. Gaseous chlorine is injected into the foot of the evaporator tube. The initiator, in the case where it is employed, was added in liquid form, in a highly concentrated solution in CCl$_4$, by a side branch delivering into the line for introducing the vaporised reactants. The chlorination-pyrolysis products leave the reactor through a tube diametrically opposite the entry, and are then condensed, treated with aqueous NaOH to neutralise the residual chlorine and the HCl produced; after gravity separation, the organic phase is separated off from the aqueous phase and analysed by gas phase chromatography. The conditions and the test results are given in Table 4 below.

TABLE 4

| | | REFERENCE TEST, WITHOUT INITIATOR | TEST WITH INITIATOR |
|---|---|---|---|
| CONDITIONS | | | |
| temperature in the reactor | °C. | 302 | 301 |
| evaporator outlet temperature (1,2-C$_2$H$_4$Cl$_2$ + CCl$_4$ + Cl$_2$) | °C. | 143 | 145 |

TABLE 4-continued

|  |  | REFERENCE TEST, WITHOUT INITIATOR | TEST WITH INITIATOR |
|---|---|---|---|
| initiator addition |  | none | 38% weight solution in CCl$_4$ |
| mean residence time* | s | 10 | 10 |
| molar ratios of reactants |  |  |  |
| 1,2-dichloroethane | mol/mol | 1 | 1 |
| Cl$_2$ | mol/mol | 1.8 | 1.8 |
| CCl$_4$ (inert diluent) | mol/mol | 2.5 | 2.5 |
| initiator (total of its constituents) | mol/mol | 0 | 0.05 |
| initiator content of the reactants | % mol | 0 | 1.0 |
| RESULTS |  |  |  |
| distribution of the chlorination products |  |  |  |
| 1,2-dichloroethane | % mol | 22.2 | <0.1 |
| cis and trans 1,2-dichloroethylene | % mol | 1.0 | 28.8 |
| 1,1,2-trichloroethane | % mol | 40.8 | 4.0 |
| trichloroethylene | % mol | 1.2 | 39.3 |
| 1,1,1,2-tetrachloroethane | % mol | 14.0 | 9.5 |
| 1,1,2,2-tetrachloroethane | % mol | 16.8 | 6.8 |
| perchloroethylene | % mol | <0.1 | 5.9 |
| pentachloroethane | % mol | 3.9 | 5.6 |
| conversion of 1,2-C$_2$H$_4$Cl$_2$ | % | 78 | >99.9 |
| degree of chlorination** | mol/mol | 1.18 | 1.79 |
| degree of dehydrochlorination*** | mol/mol | 0.02 | 0.74 |

*mean residence time = $\frac{\text{reactor volume}}{\text{volume flow rate of the reactants (at the reaction temperature)}}$

**degree of chlorination = $\frac{\text{moles of chlorine which has reacted with 1,2-dichloroethane}}{\text{moles of 1,2-dichloroethane employed}}$

***degree of dehydrochlorination = $\frac{\text{moles of unsaturated compounds}}{\text{moles of the total of compounds containing 2 carbon atoms}}$ From the results in Table 4 it can be concluded that at approximately 300° C. there is a relatively high chlorination without an initiator.

Chief products are saturated compounds such as 1,1,2-trichloroethane and 1,1,1,2- and 1,1,2,2-tetrachloroethanes.

The injection of 1 mol % of initiator produces the following effects:

increase in the degree of chlorination from 1.18 to 1.79, which corresponds to a virtually total consumption of chlorine;

increase in the degree of dehyrochlorination from 0.02 to 0.74 mol/mol, that is to say the principal products are unsaturates: cis and trans 1,2-dichloroethylene and trichloroethylene.

EXAMPLE 7

In this example a series of tests of the pyrolytic dehydrochlorination of 1,2-dichloroethane is carried out under pressure in order to illustrate the initiating action of the products of chlorination of hexachlorobutadiene.

These tests were carried out at 12 atmospheres in a tubular reactor made of stainless steel containing carbon, 320 mm in length and with an inner diameter of 20 mm. The reactor contains a thermocouple sheath 10 mm in outer diameter, situated in the middle of the reactor.

The working volume of the reactor is 7.5 cm$^3$. Preheating of the reactant from ambient temperature to the required reaction temperature, and its vaporisation, are produced by a preheater, 10 cm$^3$ in volume, mounted at the reactor inlet.

Electrical resistors whose powers can be regulated ensure uniform heating along the reactor.

The reactor is supplied with pure (>99.98%) 1,2-dichloroethane containing either an initiator [mixture C (tests 1, 2, 3, 4, 8, 9)] in solution, by means of a metering pump delivering at a known and constant rate, or without initiator (tests 5, 6 and 8).

The maintenance of the reactor at a constant pressure and the pressure reduction of the gases leaving the reaction zone to atmospheric pressure are ensured by an automatic control valve.

The HCl produced is brought down in a scrubber sprayed with water. A large part of the unconverted 1,2-dichloroethane is to be found at the foot of the scrubber. The uncondensed gases consist chiefly of vinyl chloride.

The liquid or gaseous organic phases are analysed by gas phase chromatography. The HCl produced is titrated. These determinations make it possible to establish the degrees of pyrolysis attained at various temperatures, with the initiators based on chlorinated product according to the invention and, by way of comparison, in the absence of initiator.

The results obtained are collated in Table 5. The residence time referred to corresponds to the volume of the oven divided by the volume of the gaseous reactants at the test temperature and pressure. The latter are classified in the order of increasing temperature.

Just as in the tests at atmospheric pressure, described in Example 1, a remarkable acceleration of the reaction is observed in the presence of the products of chlorination of hexachloro-1,3-butadiene; degrees of pyrolysis close to 50% are obtained between 350° and 375° C., while, in the absence of initiator (tests whose numbers are followed by the letter R) a temperature of 480° C. must be attained in order to obtain a comparable degree of pyrolysis.

TABLE 5

| Test No. | Temperature °C. | Residence time, s | Initiator, weight % | Degree of pyrolysis % |
|---|---|---|---|---|
| 1 | 323 | 10.0 | 1% mixture C | 37 |
| 2 | 349 | 10.0 | " | 48 |
| 3 | 375 | 10.0 | " | 54 |
| 4 | 400 | 10.1 | " | 55 |
| 5 | 400 | 10.0 | " | 13 |
| 6 | 439 | 10.0 | — | 19 |

TABLE 5-continued

| Test No. | Temperature °C. | Residence time, s | Initiator, weight % | Degree of pyrolysis % |
|---|---|---|---|---|
| 7 | 452 | 10.1 | 1% mixture C | 67 |
| 8 | 480 | 11 | — | 53 |

I claim:

1. Process for the pyrolytic dehydrochlorination of haloalkanes in the presence of a chlorinated product serving as a radical initiator, characterised in that the radical initiator used comprises decachlorobutane or an octachlorobutene or a mixture thereof.

2. Process according to claim 1, characterised in that the radical initiator results from the additive chlorination of hexachloro-1,3-butadiene.

3. Process according to claim 1, characterised in that the dehydrochlorination is carried out at a temperature above 200° C.

4. Process according to claim 1, characterised in that the initiator is used in a quantity of the order of 1% of the weight of the haloalkane employed.

5. Process according to claim 1, characterised in that it is applied to the manufacture of vinyl chloride by the pyrolytic dehydrochlorination of 1,2-dichloroethane.

6. Process according to claim 1, characterised in that it is applied to the manufacture of vinylidene chloride by the pyrolytic dehydrochlorination of 1,1,2-trichloroethane.

7. Process according to claim 1, characterised in that it is applied to the manufacture of trichloroethylene by the pyrolytic dehydrochlorination of 1,1,2,2-tetrachloroethane or of 1,1,1,2-tetrachloroethane.

8. Process according to claim 1, characterised in that it is applied to the manufacture of vinylidene fluoride by the pyrolytic dehydrochlorination of 1-chloro-1,1-difluoroethane.

9. The process of claim 1 in which the octachlorobutene is octachloro-1-butene.

* * * * *

UNITED STATES PATENT AND TRADEMARK OFFICE
CERTIFICATE OF CORRECTION

PATENT NO. : 4,613,709
DATED : September 23rd, 1986
INVENTOR(S) : James Franklin It is certified that error appears in the above-identified patent and that said Letters Patent is hereby corrected as shown below:

Column 9, line 66, replace "tests 1, 2, 3, 4, 8, 9" with --tests 1, 2, 3, 4, 7--.

line 68, replace "tests 5, 6 and 8" with --tests 5R, 6R and 8R--.

Column 10 table 5, in the first column labeled "Test No.", replace "5" with --5R--; replace "6" with --6R--; replace "8" with --8R-- and in the fourth column labeled "Initiator weight %", for test "5R", replace " [quote] with - [dash].

Signed and Sealed this

Twenty-second Day of November, 1988

Attest:

DONALD J. QUIGG

*Attesting Officer*   *Commissioner of Patents and Trademarks*